(12) United States Patent
Stenman

(10) Patent No.: US 6,632,623 B1
(45) Date of Patent: Oct. 14, 2003

(54) IMMUNOASSAY FOR QUANTITATIVE DETERMINATION OF THE COMPLEX BETWEEN PROSTATE SPECIFIC ANTIGEN (PSA) AND $\alpha_2$-MACROGLOBULIN ($A_2M$) IN A SAMPLE

(76) Inventor: Ulf-Håkan Stenman, Heikelsvägen 10, Grankulla (FI)

( * ) Notice: Subject to any disclaimer, the term of this patent is extended or adjusted under 35 U.S.C. 154(b) by 0 days.

(21) Appl. No.: 09/700,586
(22) PCT Filed: May 3, 1999
(86) PCT No.: PCT/FI99/00363
§ 371 (c)(1),
(2), (4) Date: Jan. 10, 2001
(87) PCT Pub. No.: WO99/61915
PCT Pub. Date: Dec. 2, 1999

(30) Foreign Application Priority Data

May 28, 1998 (FI) .................................................. 981186

(51) Int. Cl.$^7$ ............................................. G01M 33/53
(52) U.S. Cl. ....................................................... 435/7.9
(58) Field of Search ................................ 435/7.1, 7.23, 435/7.4, 7.92, 7.94, 7.9; 424/184.1; 436/501, 504, 512, 536

(56) References Cited

FOREIGN PATENT DOCUMENTS

| DE | 197 17 436 A1 | 10/1998 |
|---|---|---|
| EP | 0 196 846 | * 3/1985 |
| WO | WO 92/01936 A1 | 2/1992 |
| WO | WO 98/32021 A1 | 7/1998 |

OTHER PUBLICATIONS

Tewari, P. et al. (1995). "Immunological characterization and quantitation of prostate specific antigen–α2–macroglobulin complex in prostate cancer patient sera", *Clin. Chem.* 41(6):226.

Zhou, A.M. et al. (1993). "Multiple Forms of Prostate–Specific Antigen in Serum: Differences in Immunorecognition by Monoclonal and Polyclonal Assays," *Clin. Chem.* 39(12):2483–91.

Zhang, W–M. et al. (1998). "Characterization and immunological determination of the complex between prostate–specific antigen and α2–macroglobulin," *Clin. Chem.* 44(12), 2471–79.

Chekhonin, V.P. et al. (1997). "Identification physico–chemical properties and immunochemical characteristics of prostate specific antigen and its complexes with protease inhibitors," *Vopr. Med. Khim.* 43(3):165–71 (May–Jun.) (article in Russian, abstract in English).

Chen, Z. et al. (1996). "Addition of Purified Prostate Specific Antigen to Serum from Female Subjects: Studies on the Relative Inhibition by α2–Macroglobulin and α1–Antichymotrypsin," *J. Urol.* 156:1357–63.

España, F. et al. (1996). "Quantitative immunoassay for complexes of prostate–specific antigen with α2–macroglobulin." *Clin. Chem.* 42:545–50.

Heeb, M.J. et al. (1995). "Prostate Specific Antigen–α2–Macroglobulin Complexes in Prostate Cancer Patient Sera," *Biochem. Mol. Biol. Int.* 37:917–23.

Lilja, H. et al. (1999). "Significance and metabolism of complexed and noncomplexed prostate specific antigen forms, and human glandular kallikrein 2 in clinically localized prostate cancer before and after radical prostatectomy," *J. Urol.* 162:2029–34.

* cited by examiner

*Primary Examiner*—Susan Ungar
*Assistant Examiner*—Minh-Tam Davis
(74) *Attorney, Agent, or Firm*—Rothwell, Figg, Ernst & Manbeck (57) ABSTRACT

This invention concerns an immunoassay for quantitative determination of the amount of the complex (PSA-$A_2$M) between prostate specific antigen (PSA) and $\alpha_2$-macroglobulin ($A_2$M) in a sample. The assay comprises the steps of removing immunoreactive PSA from the sample, treating the PSA-$A_2$M complex in the remaining supernatant so as to make the PSA thereof immunoreactive, determining the immunoreactive PSA derived from the PSA-$A_2$M complex by exposing it to an antibody which binds immunoreactive PSA, and detecting the PSA. The invention also concerns a method for differentiating patients with cancer of the prostate (PCa) from patients with benign prostatic hyperplasia (BPH) or healthy male subjects without PCa, wherein the individual's body fluid concentration of PSA has been determined as free PSA and as total PSA. The method is characterized in that PSA complexed with $A_2$M (PSA-$A_2$M) in the individual's serum sample has been determined, and that the ration between PSA-$A_2$M and other forms of PSA is calculated, or that the diagnostic value is calculated by logistic regression, neural networks, fussy logic or similar mathematical and statistical methods using PSA-$A_2$M and other forms of PSA, such as total PSA, free PSA and PSA-ACT as input variables.

15 Claims, 7 Drawing Sheets

IMMUNOASSAY FOR QUANTITATIVE DETERMINATION OF THE COMPLEX BETWEEN PROSTATE SPECIFIC ANTIGEN (PSA) AND $\alpha_2$-MACROGLOBULIN ($A_2M$) IN A SAMPLE

CROSS-REFERENCE TO RELATED APPLICATION

The present application is a national stage filing under 35 U.S.C. §371 of PCT/F199/00363 filed on May 3, 1999. The present application further claims priority under 35 U.S.C. §119(d) to Finnish Patent Application No. 981186 filed on May 28, 1998.

FIELD OF THE INVENTION

This invention relates to an immunoassay for the quantitative determination of the amount of the complex (PSA-$A_2M$) between prostate specific antigen (PSA) and $\alpha_2$-macroglobulin ($A_2M$) in a serum sample. The invention relates further to an improved method for differentiating patients with cancer of the prostate (PCa) from patients with benign prostatic hyperplasia (BPH) or healthy male subjects without PCa.

BACKGROUND OF THE INVENTION

The publications and other materials used herein to illuminate the background of the invention, and in particular, cases to provide additional details respecting the practice, are incorporated by reference.

In the following description, the abbreviation "PSA" means prostate-specific antigen; $A_2M$ $\alpha_2$-macroglobulin; PSA-$A_2M$ complex between PSA and $A_2M$; ACT $\alpha_1$-antichymotrypsin; PSA-ACT complex between PSA and ACT; API $\alpha_1$-protease inhibitor; PSA-API complex between PSA and API; MAb monoclonal antibody; BSA bovine serum albumin; TBS 50 mmol/L Tris-HCl buffer, pH 7.4 containing 150 mmol/L sodium chloride and 8 mmol/L sodium azide; IFMA immunofluorometric assay; SDS sodium dodecyl sulfate; SDS-PAGE: SDS polyacrylamide gel electrophoresis; BPH benign prostatic hyperplasia; PCa prostate cancer; CV coefficient variation; ROC receiver operating characteristic; AUC area under the curve; and sandwich assay for PSA-$A_2M$ a sandwich assay using a monoclonal anti-PSA antibody as catcher and a labelled antibody to $A_2M$ for detection.

In the definition of the invention and in the results disclosed below, the term "total PSA" shall be understood to mean the total amount of immunodetectable PSA in a sample before any denaturation or other treatment of the sample to render other, under normal conditions non-immunodetectable forms of PSA immunodetectable.

Prostate-specific antigen (PSA) is a 30 kDa single chain glycoprotein mainly produced by prostatic epithelium (1–3). It is a serine protease with chymotrypsin-like enzymatic activity and a member of the glandular kallikrein family (4–6). In vitro PSA forms complexes with protease inhibitors such as $\alpha_2$-macroglobulin ($A_2M$), pregnancy zone protein, $\alpha_1$-antichymotrypsin (ACT), $\alpha_1$-protease inhibitor (API) and protein C inhibitor (6–9).

In serum most of the immunoreactive PSA occurs in complex with ACT (PSA-ACT), while the rest is either free or in complex with API (PSA-API) (10–12). Five major antigenic regions have been identified on the PSA molecule and only one of them is covered by ACT in PSA-ACT (13). The PSA-ACT and PSA-API complexes can be readily detected by specific sandwich assays or by conventional PSA immunoassays (9, 10, 14). Specific measurement of complexed and free PSA in serum improves the diagnostic accuracy for prostate cancer (PCa) compared to assay of total PSA (10, 12, 14, 15).

$A_2M$ is a tetramer assembled from pairwise disulfate-bridged 180 kDa subunits (16, 17). Binding of proteases to $A_2M$ is initiated by a proteolytic attack of the bait region of $A_2M$ resulting in a comformational change and entrapping of the enzyme within the $A_2M$ molecule (18). This sterically hinders access of high molecular weight substance such as high molecular weight inhibitors or antibodies to the enzymes (19). The PSA-$A_2M$ complex is not detected by conventional PSA immunoassays (8, 11). When PSA-$A_2M$ is denatured with sodium dodecyl sulfate (SDS), PSA epitopes are exposed rendering it reactive with PSA antibodies (11, 20). PSA-$A_2M$ has been qualitatively detected in male serum with high levels of PSA by immunoblotting after SDS polyacrylamide gel electrophoresis (SDS-PAGE) (20).

The design of two-site immunoassays for the determination of circulating PSA-$A_2M$ complexes have recently been reported (27 and 31). These assys combine antibodies recognizing epitopes on PSA with antibodies recognizing epitopes on $A_2M$ (the native and/or the transformed molecule). Such assays are feasible since some epitopes of PSA, while in complex with $A_2M$, are still to some extent accessible to certain anti-PSA antibodies. It is also possible to enhance this recognition by partly denaturing the PSA-$A_2M$ complex e.g. by the use of SDS treatment. However, the analytical sensitivities using these assays are still clearly inferior compared to state-of art assays of circulating free, ACT-complexed or total PSA assays, which fact is explained by the poor accessability of anti PSA antibodies to PSA in complex with $A_2M$. The large excess of free $A_2M$ or $A_2M$ complexed to other serpines may also introduce non-specific interferences with the potential appearance of false signal elevations unrelated to the presence of PSA-$A_2M$.

The International Patent Publication WO 92/01936 (30) discloses the use of the ratio between free PSA and total PSA, between a PSA-proteinase inhibitor complex and total PSA, or between free PSA and PSA-proteinase inhibitor complex, as a marker to distinguish between PCa and BPH. As one of the PSA-proteinase inhibitor complexes is mentioned PSA-$A_2M$. However, no method for its detection was described.

OBJECT AND SUMMARY OF THE INVENTION

The object of the present invention is to provide a novel sensitive method for the quantitative determination of the PSA-$A_2M$ complex in an individual's serum sample.

Another object of the invention is to provide an improved method for differentiating PCa patients from BPH patients or healthy male subjects without PCa, based on the use of a new marker comprising the information on the amount of the PSA-$A_2M$ complex in an individual's serum sample.

Thus, according to one aspect, this invention concerns an immunoassay for quantitative determination of the amount of the complex (PSA-$A_2M$) between prostate specific antigen (PSA) and $\alpha_2$-macroglobulin ($A_2M$) in a sample. Said method is characterized by the steps of removing the immunoreactive PSA from said sample,
treating the PSA-$A_2M$ complex in the remaining supernatant so as to make the PSA thereof immunoreactive,
determining the immunoreactive PSA derived from the PSA-$A_2M$ complex by exposing it to an antibody which binds said immunoreactive PSA, and
detecting said PSA.

Furthermore, this invention concerns a method for differentiating patients with cancer of the prostate (PCa) from patients with benign prostatic hyperplasia (BPH) or healthy male subjects without PCa, wherein the individual's body fluid concentration of prostate specific antigen (PSA) has been determined as free PSA and as total PSA. Said method is characterized in that PSA complexed with $A_2M$ (PSA-$A_2M$) in the individual's serum sample has been determined, and that the ratio between PSA-$A_2M$ and other forms of PSA is calculated, or that the diagnostic value is calculated by logistic regression, neural networks, fuzzy logic, or similar mathematical and statistical methods, using PSA-$A_2M$ and other forms of PSA, such as total PSA, free PSA and PSA-ACT as input variables.

DETAILED DESCRIPTION OF THE INVENTION

The diagnostic validity of combinations of PSA-$A_2M$ with different forms of PSA can be estimated in an alternative way (not involving formation of ratios or products), through combination by logistic regression analysis. Logistic regression analysis of combinations such as PSA-$A_2M$, PSA-ACT, free PSA and total PSA frequently provide even better discrimination than ratios calculated from the individual measurements from each patient. Logistic regression analysis is instrumental in providing the basis for various "risk analysis systems that can provide medical decision support". Other examples of such data handling systems are: artificial neural networks (ANN), neuro fuzzy networks (NFN), multilayer perceptron (MLP), learning vector quantization (LVQ) [Freeman et al. In "Neural Networks: Algorithms, Applications and Programming Techniques by Addison-Wesley Publishing Company" 1991, Zadeh Information and Control 1965; 8:338–353, Zadeh "IEEE Trans. on Systems, Man and Cybernetics" 1973; 3:28–44, Gersho et al. In "Vector Quantization and Signal Compression by Kluywer Academic Publishers, Boston, Dordrecht, London" 1992, Hassoun "Fundamentals of Artificial Neural Networks by The MIT Press, Cambridge, Massachusetts, London" 19951].

According to a preferred embodiment of the invention, the removal of the immunoreactive PSA from the sample is made by immunoadsorption of said PSA. The supernatant obtained after removal of the immunoreactive PSA preferably is treated so as to denaturate the PSA-$A_2$M complex therein, whereby the PSA of said complex is rendered immunoreactive.

Preferably, the denaturation of the complex is performed by raising the pH of the supernatant to the range 10.5 to 12, most preferably about 11.5, by the addition of e.g. NaOH.

According to a particularly preferable embodiment, the sample is a serum sample from a male individual, and a signal from the antibody detecting the PSA derived from the PSA-$A_2$M complex is used to read the serum concentration of said PSA-$A_2$M complex from a standard curve established with calibrators consisting of PSA-$A_2$M complex prepared in vitro.

PSA is preferably determined by a sandwich assay using two monoclonal antibodies.

Preferably, the new marker used to distinguish PCa patients from BPH patients and other non-PCa individual is the ratio $$\frac{(PSA - A_2M) + \text{free } PSA}{\text{total } PSA}$$

The diagnostic impact can also be estimated using statistical methods that consider the relationship between the concentrations of the various forms of PSA.

This method is particularly useful when the individuals have total PSA in the range 2 to 20.

PSA rapidly forms a complex with $A_2$M in vitro (8, 11) and PSA-$A_2$M can be immunochemically detected in male serum by immunoblotting but not by conventional immunoassays for PSA (8, 11, 20). The assay developed is based on removal of immunoreactive PSA, i.e. PSA-ACT, PSA-API and free PSA by immunoadsorption, followed by denaturation of PSA-$A_2$M of the supernatant at high pH, and measurement of the PSA thus rendered immunoreactive. The treatment at high pH causes partial dissociation of PSA-$A_2$M. The free PSA released and that covalently bound to denatured $A_2$M can be detected by a conventional PSA immunoassay. The recovery of PSA immunoreactivity after denaturation is about 30% of the calculated PSA content in PSA-$A_2$M. As the denaturation at pH 11.5 does not cause any considerable loss of immunoreactivity of free PSA, the low recovery is probably due to reduced immunoreactivity of the PSA bound to denatured $A_2$M. This is taken into account by using PSA-$A_2$M formed in vitro for calibration of the assay.

Treatment of PSA-$A_2$M with SDS has previously been used to expose PSA encapsulated by $A_2$M (11, 20). However SDS interferes with antibody binding. This effect can be reduced by considerable dilution (26), which, however reduces the sensitivity of the assay. NaOH can be neutralized with HCl with little sample dilution. After NaOH treatment of PSA-$A_2$M and neutralization, $A_2$M was permanently denatured whereas PSA retains its immunoreactivity. With a sample volume of 225 µL, corresponding to 75 µL serum or calibrators, the detection limit was 0.14 µg/L. This enabled us to reliably analyse PSA-$A_2$M in sera with total PSA concentrations above 2–4 µg/L.

Because the same amount of PSA immunoreactivity was released after denaturation of PSA-$A_2$M formed in vitro and that occurring in serum, we used PSA-$A_2$M formed in vitro to calibrate the PSA-$A_2$M assay. In order to obtain the same buffering capacity as in serum, the calibrators were prepared by dilution of purified PSA-$A_2$M in female serum. PSA-$A_2$M was stable in female serum, thus it was a suitable matrix for the PSA-$A_2$M calibrators.

By using a sandwich assay consisting of a capture antibody to PSA and tracer antibody to $A_2$M, Espana et al. recently measured PSA-$A_2$M in serum and found that the concentration was not related to the concentration of total PSA (27). With an identical assay, we have previously detected very low levels of PSA-$A_2$M immunoreactivity in male serum with high PSA concentrations (10). In the present study we found that this apparent PSA-$A_2$M immunoreactivity is due to $A_2$M as it was also observed in purified $A_2$M in and female serum devoid of PSA. This suggests that it represents a nonspecific background caused by adsorption of $A_2$M to the solid phase. This explanation is supported by the finding that <1% of the PSA-$A_2$M in serum and that formed in vitro could be recovered by immunoadsorption using either mono- or polyclonal anti-PSA antibodies.

Denaturation of PSA-$A_2$M at high pH rendered it immunoreactive in the sandwich assay for PSA-$A_2$M as well as in the conventional PSA assay. Denaturation of pure $A_2$M at high pH also induced a response in the sandwich assay for PSA-$A_2$M which probably was due to an increased nonspecific background. This effect was not present in the new immunoassay for PSA-$A_2$M, which measured PSA released from the complex and bound to denaturated $A_2$M. This approach enabled us to quantitate PSA-$A_2$M in serum containing PSA at clinically relevant concentrations and showed that the concentration of PSA-$A_2$M in serum is correlated to total PSA and that the proportion of PSA-$A_2$M in serum is higher in BPH than in PCa.

The proportion of PSA-$A_2$M in serum of BPH patients was higher than in PCa sera. This is contrary to the proportion of PSA-ACT, which is higher in PCa (10, 14). This is probably explained by differences in the mechanism of complex formation of PSA with $A_2$M and ACT, respectively, and in their clearance from circulation. PSA forms complexes more rapidly with $A_2$M than with ACT and even the proteolytically cleaved or "nicked" PSA isoenzymes can bind to $A_2$M (8). $A_2$M-protease complexes have a half-life of only 2–5 min (17) which is much shorter than that of total PSA, i.e. 2 to 3 days (28, 29). Although most of the enzymatically active PSA released into circulation may be expected to form complexes with $A_2$M, PSA-ACT predominates in plasma because of its slow clearance. Due to the rapid complexation of enzymatically active PSA with $A_2$M (8), most of the free PSA present in blood at the time of sampling may be assumed to have low enzyme activity. It could consist of enzymatically inactive proenzyme and "nicked" isoenzymes which only bind with $A_2$M (8). Nicked PSA could gradually form complexes with $A_2$M after sampling. The presence of a high proportion of free PSA in serum from BPH patients could therefore lead to preferential formation of PSA-$A_2$M after sampling. Formation of PSA-$A_2$M in vitro is thought to cause loss of PSA immunoreactivity during long term storage of serum (14, 25).

Thus PSA-$A_2$M may reflect the concentration of free PSA at the time of sampling. This notion is actually supported by our results, which suggest that the sum of PSA-$A_2$M and free PSA in serum improves the diagnostic accuracy for PCa as compared to free PSA.

Measurement of the ratio of PSA-$A_2$M to total PSA in serum improved the diagnostic accuracy as compared to total PSA as evidenced by ROC curves analysis. The ratio ((PSA+$A_2M$)+free PSA)/total PSA gives a further improved ROC curve. We evaluated the clinical utility of this marker in a subgroup of PCa and BPH patients with serum PSA concentration range of 4–20 μg/L. The results show that the aforementioned ratio can be used to reduce many false positive results obtained by measurement of free PSA and total PSA.

The invention is described more in detail in the following experimental section.

Materials and Methods

Samples

Sera were obtained from 73 (median age 67.6 and range 50.3–96.1 year) referred patients with PCa, 58 (median age 69.6 and range 51.9–81.9 year) with BPH and 46 healthy females. The diagnosis of PCa was based on histological examination of tissues obtained by biopsy or radical prostectomy and that of BPH based on histological examination of tissues obtained by transurethral resection of the prostate. The sera were taken before initiation of therapy. All samples were kept frozen at −20° C. until analysed.

Materials

Reagents. Superdex-200 was from Pharmacia Biotech (Uppsala, Sweden), 3,3'-diaminobenzidine tetrahydrochloride from Sigma (St. Louis, Mo.), and PVDF membrane (Immobilon P) from Millipore (Bedford, Maas.). Streptavidin-conjugated magnetic beads were from Promega (Madison, Mich.). Sodium hydroxide was from Reagena LTD (Kuopio, Finland). Sulfosuccinimidyl-6-(biotinamido) hexanoate was purchased from Pierce (Rockford, Ill.). Trifluoroacetic acid was form Fluka (Buchs, Switzerland). DELFIA assay buffer and enhancement solution used in immunoassays were form Wallac (Turku, Finland).

Proteins. The major isoenzyme of PSA was purified from human seminal fluid (21) and $A_2M$ from plasma as described (22). Molecular mass protein markers were from Amersham (Little Chalfont, Buckinghamshire, England). Bovine serum albumin (BSA) was from Sigma.

Antibodies. A monoclonal antibody (MAb) to PSA (5E4) was produced by standard procedures (Leinonen et al., unpublished results), H117 and H50 were kind gifts from Abbott Diagnostics (Abbott Park, Ill.). Polyclonal antibodies to PSA and $A_2M$, and a peroxidase-conjugated swine anti-rabbit IgG immunoglobulin were from Dakopatts (Glostrup, Denmark). MAb 5E4 and the polyclonal antibody to PSA were biotinylated according to instructions of the manufacturers (Pierce). MAb H50 and the polyclonal IgG to $A_2M$ were labeled with Eu as described (10).

Experimental procedures

Immunoassays. Total PSA was determined by a time-resolved immunofluorometric assay (IFMA) using MAb H117 as capture and MAb H50 labeled with Eu as tracer. The calibrators were prepared from pure PSA and standardized as described (21). A sandwich assay for PSA-$A_2M$ was constructed by using the polyclonal antibody to PSA coated on the solid phase and a polyclonal antibody to $A_2M$ labeled with Eu as tracer (10). The IFMA for $A_2M$ was performed as described (8).

Gel filtration. A Superdex-200 column (60×1.6 cm) was used and eluted with 50 mmol/L Tris-HCl buffer, pH 7.4 containing 150 mmol/L sodium chloride and 8 mmol/L sodium azide (TBS). Flow rate was 15 mL/h and 2-mL fractions were collected. The column was roughly calibrated by measuring the absorbance at 280 nm in the fractions to identify the elution volumes of human IgG (150 kDa) and human albumin (68 kDa).

Electrophoresis and immunoblotting. SDS-PAGE was performed under reducing conditions (23) in 10×10 cm, 2 mm thick, 3–16% gradient polyacrylamide gels. Proteins transferred eletrophoretically to immobilon P were incubated with polyclonal antibodies to PSA or $A_2M$ (24). Bound antibodies were detected with peroxidase-conjugated swine anti-rabbit IgG immunoglobulin using 3,3'-diaminobenzidine tetrahydrochloride as a substrate.

Complex formation between PSA and $A_2M$. Sixty μg of purified PSA was incubated with 12 mg $A_2M$ in 800 μL TBS (1:10 molar ratio) at 37° C. Aliquots of 100 μL were taken at time intervals of 0, 1, 3, 6, 8, 24, 48 and 72 h. The aliquot taken at 72 h was subjected to gel filtration. The fractions obtained and the aliquots were further analysed by immunoassays for PSA, $A_2M$, PSA-$A_2M$ and by immunoblotting.

Immunoadsorption of PSA. Five μg of biotinylated MAb to PSA (5E4) was incubated with 100 μg streptavidin conjugated magnetic beads at 25° C. After 30 min, unbound antibodies were removed by washing the beads with assay buffer. The beads (100 μg) were incubated with 200 μL of PSA-$A_2M$ formed in vitro or male serum at 25° C. After 30 min, the beads were collected with a magnet and the supernants were analysed for PSA and PSA-$A_2M$.

Denaturation of PSA-$A_2M$. PSA-$A_2M$ formed in vitro was separated from free PSA by gel filtration, diluted in assay buffer containing 5% BSA and incubated with sodium hydroxide (NaOH) at a final concentration of 0–100 mmol/L. Aliquots withdrawn at 10, 30, 60 and 180 min were separated by gel filtration and analysed by the IFMA for PSA. As a control, purified PSA diluted in the assay buffer containing 5% BSA was treated in the same way. In addition, 10 sera with high levels of PSA (>20 μg/L) from patients with PCa were incubated with NaOH after immunoadsorption of PSA as described above.

Assay of PSA-$A_2M$ in serum. Calibrators or serum samples (200 μL) were subjected to immunoadsorption and 180 μL of adsorbed calibrators or samples were incubated with 20 μL NaOH (0.6 mol/L) at 25° C. After 30 min, 340 μL of assay buffer containing 20 μL of hydrochloric acid (0.6 mol/L) was added for neutralization. Duplicates of 225 μL, corresponding to 75 μL of original serum, were assayed for total PSA by IFMA. The intra- and inter-assay coefficients variation (CV) was determined by measuring five serum samples with PSA-$A_2M$ concentrations ranging from 0.5 to 10 μg/L 10 times within the same or different runs, respectively.

Standardization of the PSA-A2M immunoassay. The content of PSA in the PSA-$A_2M$ standard was estimated by calculating the loss of PSA immunoreactivity after reaction of free PSA with $A_2M$. The mixture containing PSA, $A_2M$ and PSA-$A_2M$ was separated by gel filtration and the PSA concentration was easured in the fractions by IFMA. The calibrators were prepared by dilution of purified PSA-$A_2M$ formed in vitro in a pool of female serum to concentrations of 0, 0.1, 1, 4, 20, and 100 μg/L. The stability of purified PSA-$A_2M$ was tested by measuring the concentrations of PSA and PSA-$A_2M$ after storage of PSA-$A_2M$ in female serum at 4 or 25° C. for 0, 24, 72, 120 and 168 h.

Statistical Analysis

The detection limit of the PSA-$A_2M$ assay was defined as the concentration giving a fluorescence signal equal to that of a female serum pool plus 2 SD (calculated from 20 duplicates). The difference in the concentrations and proportions of PSA-$A_2M$ between serum from patients with PCa and BPH was tested by the Wilcoxon rank sum test. The diagnostic accuracy of the various PSA assays were compared by receiver operating characteristic (ROC) curves analysis as described (25).

Results

Formation and characterization of PSA-A$_2$M

Figure 1:
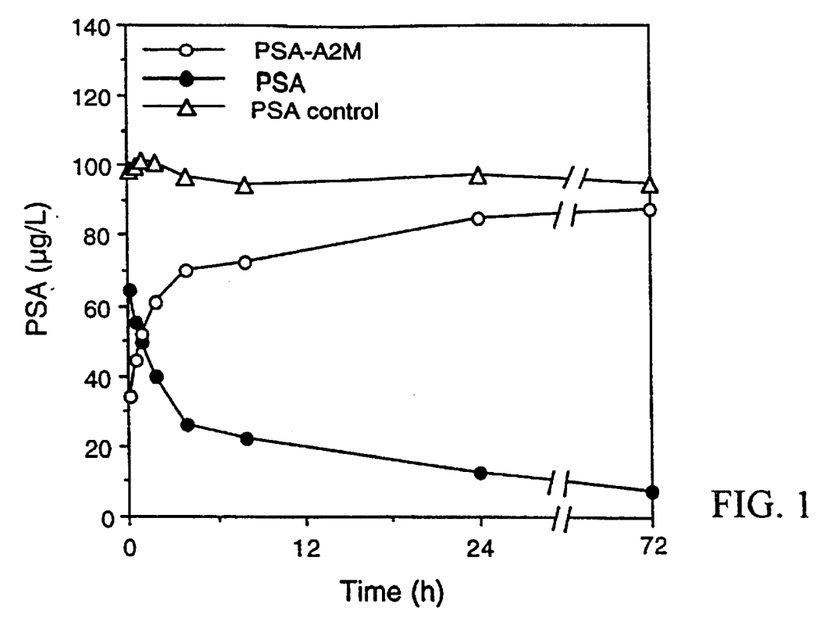
FIG. 1 shows kinetics of the formation of PSA-$A_2M$ in vitro. Sixty μg PSA in 100 μL TBS was incubated with 12 mg $A_2M$ (1:10 molar ratio) in 700 μL TBS at 37° C. Aliquots of 100 μL were drawn at time intervals of 0, 1, 3, 6, 8, 24, 48 and 72 h, and analysed by the IFMA for PSA and by the assay for PSA-$A_2M$. A control containing pure PSA diluted in TBS was stable under the conditions used.
Figure 2:
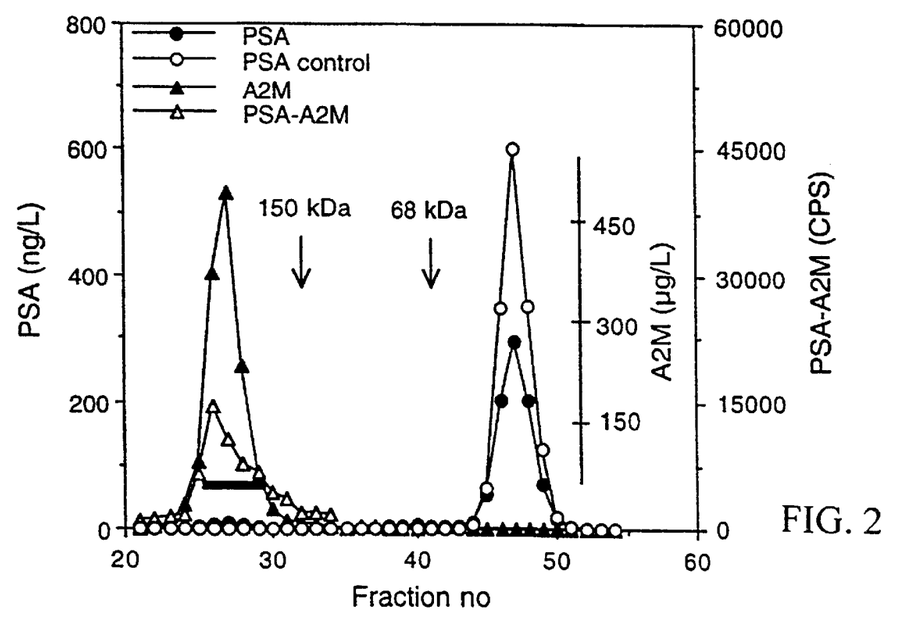
FIG. 2 shows separation of PSA-$A_2M$ formed in vitro by gel filtration. Sixty μg PSA and 12 mg $A_2M$ (1:10 molar ratio) were incubated in 800 μL of TBS at 37° C. for 72 h and fractionated by gel filtration on a Superdex-200 column. The horizontal bar indicates fractions further characterized by immunoblotting and immunoadsorption. The elution pattern of pure PSA (open circles) is shown in comparison. The other curves show the concentrations in the various fractions of PSA measured by IFMA (closed circles), total $A_2M$ measured by IFMA (open triangles) and the PSA-$A_2M$ complex measured by the novel IFMA.

Formation of PSA-A2M in vitro. Incubation of purified PSA with A$_2$M at 37° C. resulted in a gradual loss of immunoreactive PSA detected by the PSA IFMA (FIG. 1). Gel filtration of the aliquot obtained at the 72 h time point showed that very little PSA immunoreactivity (<1% of added PSA) was detected in the fractions containing A$_2$M though about 40% of the PSA added had complexed with A$_2$M (FIG. 2). By the sandwich assay (10) for PSA-A$_2$M a low response was observed in the fractions containing A$_2$M (FIG. 2). However, a similar response was also detected after gel filtration of pure A$_2$M or female serum without PSA immunoreactivity (not shown). The fractions containing A$_2$M obtained by gel filtration were further subjected to immunoadsorption with biotinylated mono- and polyclonal PSA antibodies and streptavidin conjugated magnetic beads. Only trace amounts of immunoreactive PSA (<1%) were adsorbed to the magnetic beads. Elution of the adsorbed material with trifluoroacetic acid and immunoblotting with polyclonal anti-PSA or -A$_2$M antibodies showed that the immunoreactive PSA was in free form, and no A$_2$M immunoreactivity was associated with this PSA (not shown).

Figure 3:
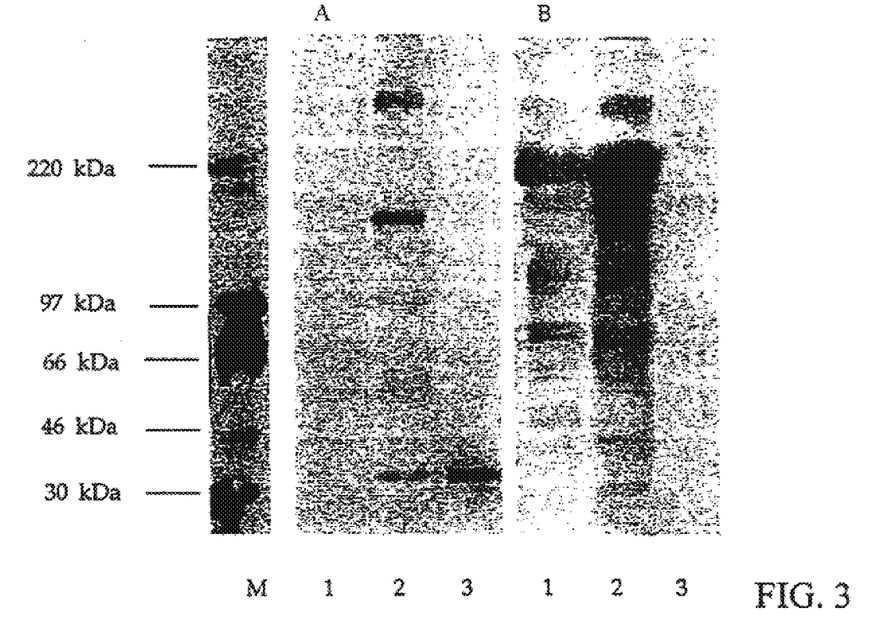
FIG. 3 shows identification of PSA-$A_2M$ formed in vitro by immunoblotting. The fractions containing $A_2M$ obtained by gel filtration as indicated in FIG. 2 were pooled and subjected to SDS-PAGE and immunoblotting with polyclonal anti-PSA (Panel A) and -$A_2M$ (Panel B) antibodies. Lane M: molecular mass markers as following: Myosin (220 kDa), phosphorylase (97 kDa), bovine serum albumin (66 kDa), ovalbumin (46 kDa), carbonic anhydrase (30 kDa). Lane 1: purified $A_2M$. Lane 2: PSA-$A_2M$ purified by gel filtration. Lane 3: purified PSA.

Characterization of PSA-A$_2$M by immunoblotting. When the fractions containing A$_2$M obtained by gel filtration were analysed by SDS-PAGE and immunoblotting, two bands with Mr of 300–400 and 100–150 kDa reacting with PSA and A$_2$M antibodies were observed (FIG. 3 A and B). The band of 300–400 kDa apparently represented dimeric A$_2$M complexed with PSA, and the band of 100–200 may represent monomeric A$_2$M complexed with PSA. Several bands of Mr <100 kDa reacted only with antibodies to A$_2$M, suggesting that they represent fragments of A$_2$M (FIG. 3 B). In addition, a weak band of 30 kDa reacting with PSA antibody was also observed (FIG. 3 A), indicating that a minor portion of PSA was released from PSA-A$_2$M by treatment with SDS. Endogenous PSA-A$_2$M in serum displayed similar bands reacting with antibodies to PSA or A$_2$M. Adsorption with PSA antibody did not remove the PSA or A$_2$M-immunoreactivity from the PSA-A$_2$M fractions (not shown).

Figure 4:
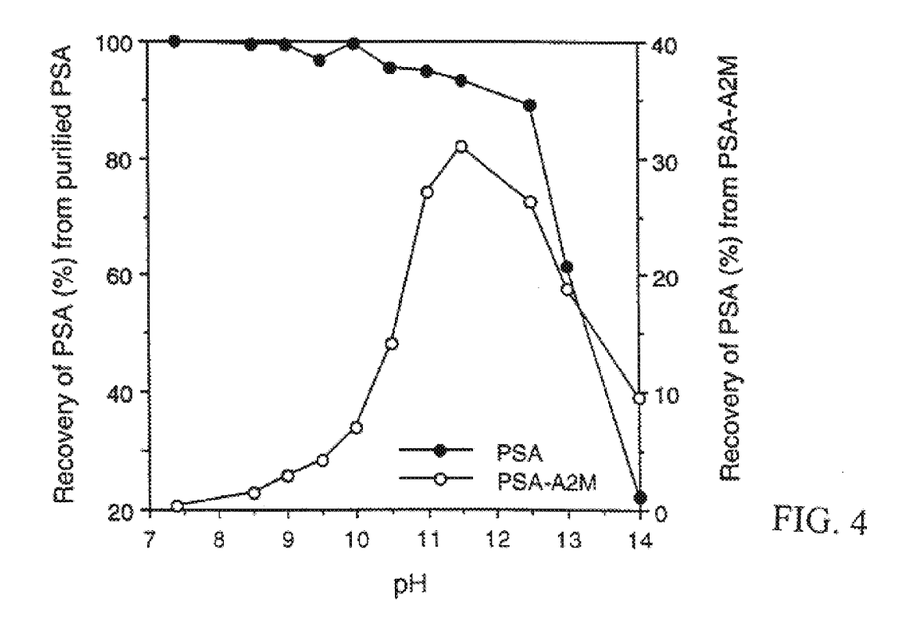
FIG. 4 shows the release of PSA immunoreactivity from PSA-$A_2M$ formed in vitro at various pH values. PSA-$A_2M$ purified by gel filtration was diluted in assay buffer containing 5% BSA and incubated with NaOH at a final concentration ranging between 0 and 100 mmol/L at 25° C. for 30 min. The aliquots were analysed with the PSA IFMA. The control consisted of pure PSA diluted in the same buffer as above.

Denaturation of PSA-A2M. After incubation of PSA-A$_2$M at high pH and neutralization, PSA immunoreactivity was measurable by the PSA IFMA. The recovery of PSA immunoreactivity increased with increasing pH up to 11.5 (FIG. 4), corresponding to a NaOH concentration of 70 mmol/L. The maximal recovery of PSA immunoreactivity was about 30% of the calculated PSA content in PSA-A$_2$M. Incubation of PSA-A$_2$M at pH 11.5 for 2 h at 25° C. only marginally affected the recovery of PSA immunoreactivity (not shown). Incubation of purified PSA at increasing pH tended to reduce PSA immunoreactivity, but the loss was remarkable only at pH values above 12.5 (FIG. 4).

Figure 5:
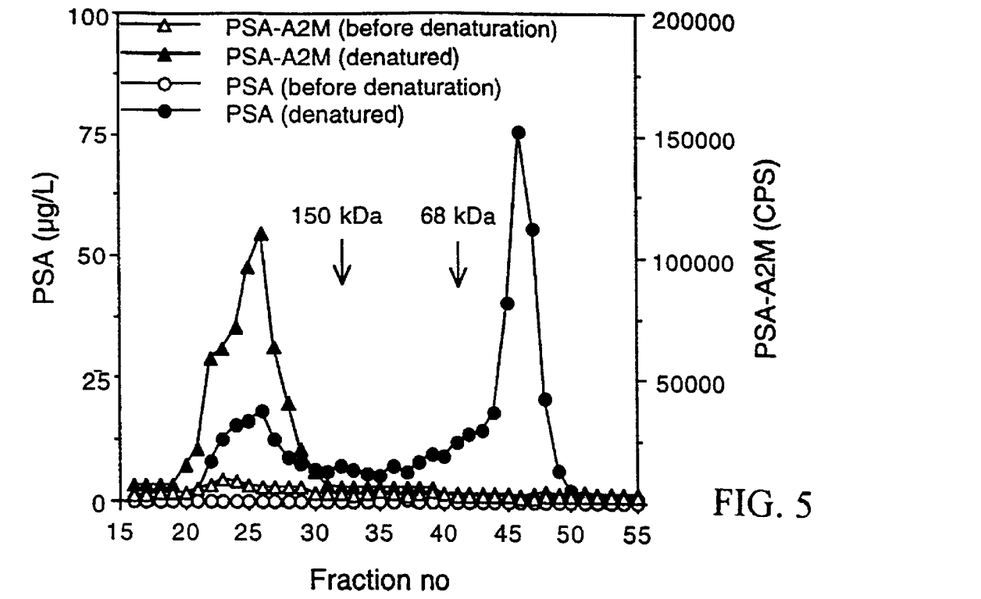
FIG. 5 shows separation of PSA-$A_2M$ formed in vitro by gel filtration after denaturation at pH 11.5. Purified PSA-$A_2M$ formed in vitro was incubated at pH 11.5 for 30 min at 25° C. The samples before and after treatment were fractionated by gel filtration. Closed triangles: PSA-$A_2M$ in fractions measured with the novel assay for PSA-$A_2M$ after denaturation; Open triangles: PSA-$A_2M$ in fractions measured with the sandwich assay for PSA-$A_2M$ before denaturation; Closed circles: PSA measured by PSA IFMA after denaturation; Open circles: PSA measured by the PSA IFMA before denaturation.

When PSA-A$_2$M formed in vitro was incubated at pH 11.5 and subjected to gel filtration, two components were detected by the PSA IFMA (FIG. 5). A high molecular weight peak (~400 kDa) comprised about 30% of the total PSA immunoreactivity recovered whereas the rest eluted as a 30 kDa component (FIG. 5). The 400 kDa component was also detected by the sandwich assay for PSA-A$_2$M (not shown), suggesting that it represented PSA bound to denaturated A$_2$M. The 30 kDa peak of PSA immunoreactivity apparently consisted of free PSA released from PSA-A$_2$M (FIG. 5). When added to female serum, the released PSA was able to further form a complex with A$_2$M and ACT, indicating that it was enzymatically active (not shown).

Treatment of immunoadsorbed serum from PCa patients at high pH caused appearance of PSA immunoreactivity detected by the PSA IFMA. Maximal recovery was obtained at pH 11.5. Gel filtration of the NaOH-treated serum revealed a high molecular weight component (~400 kDa) and a 30 kDa component containing about 30% and 70% of recovered PSA immunoreactivity, respectively. The smaller component was detected only by PSA IFMA while the 400 kDa component was also detected by the sandwich assay for PSA-A$_2$M (not shown). Thus PSA-A$_2$M formed in vitro and endogenous PSA-A$_2$M in serum showed similar patterns after denaturation at high pH.

Immunoassay for PSA-A$_2$M

Immunoadsorption of PSA in serum. Immunoadsorption of PCa serum with PSA antibody removed more than 99.9% of PSA immunoreactivity if the concentration of PSA in serum was below 500 μg/L. After washing with assay buffer, the PSA immunoreactivity was eluted from the beads with 0.1% trifluoroacetic acid and subjected to SDS-PAGE and immunoblotting. The extracted PSA consisted of complexed PSA (90 kDa) and free PSA. No A$_2$M immunoreactivity was detected (not shown).

Figure 6:
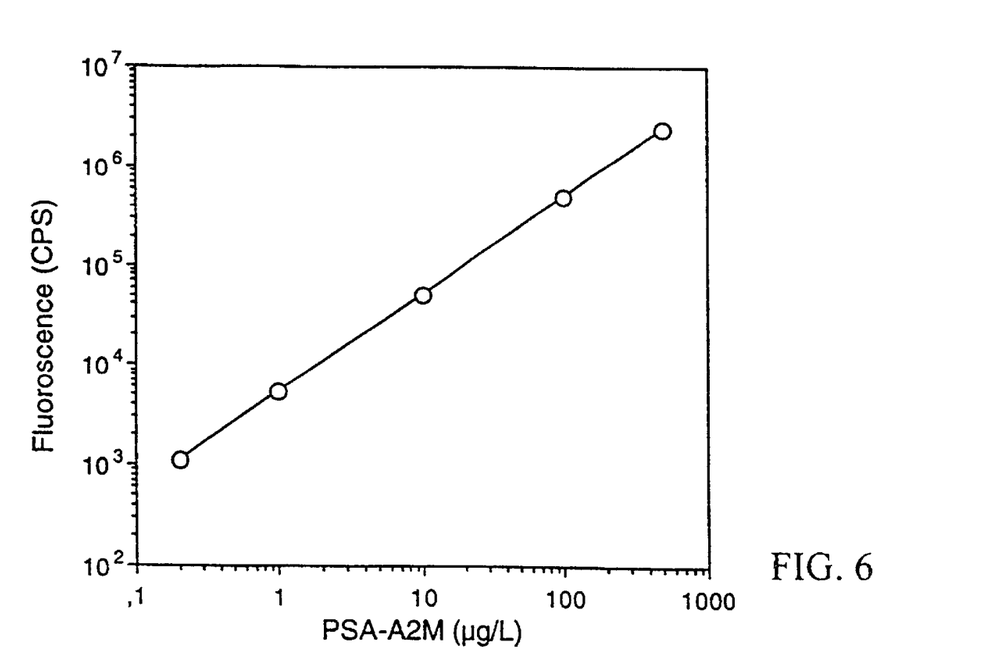
FIG. 6 represents a standard curve for the immunoassay of PSA-$A_2M$. The calibrators were prepared by dilution of purified PSA-$A_2M$ formed in vitro in female serum. The background of about 500 cps has been subtracted.

Immunoassay for PSA-A2M. An immunoassay for PSA-A$_2$M was constructed by using immunoadsorption, treatment at pH 11.5 and determination of the released PSA immunoreactivity. The measuring range was 0–100 μg/L (FIG. 6) and the detection limit 0.14 μg/L. The intra-assay CV was 4–9% and the inter-assay CV% 8–14%. When PSA-A$_2$M was added to female serum and stored for 7 days at 4° C. the recovery was 97%, and at 25° C. it was 95%. No PSA immunoreactivity was detected by the IFMA for PSA before denaturation.

Figure 7:
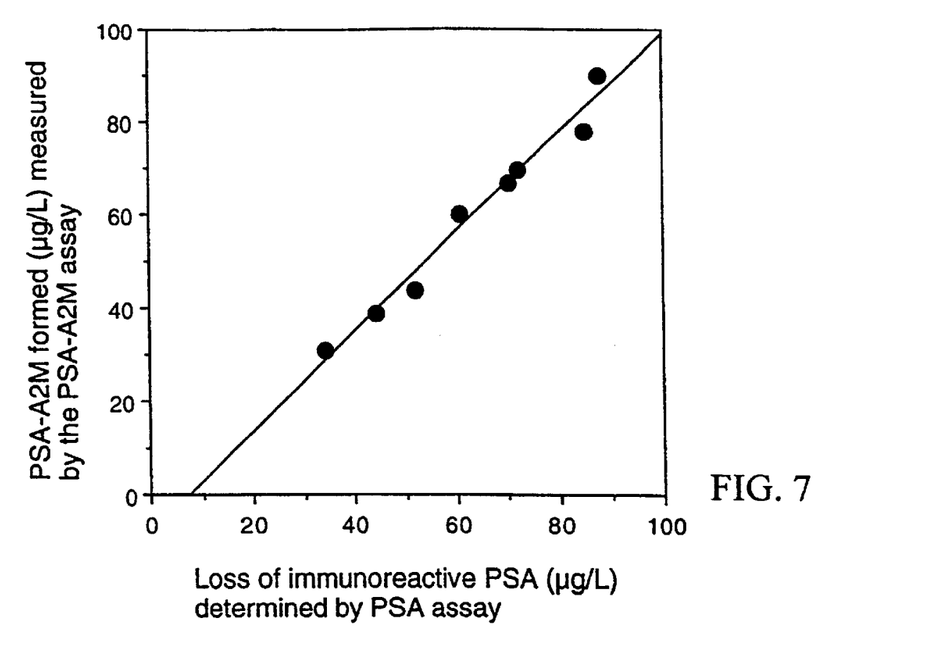
FIG. 7 shows the correlation between the loss of PSA immunoreactivity and PSA-$A_2M$ formation when PSA was incubated with $A_2M$ in vitro. Purified PSA was incubated with $A_2M$ at 37° C. as indicated in FIG. 1. Aliquots drawn at 0, 1, 3, 6, 8, 24, 48 and 72 h were analysed by the PSA IFMA and the novel assay for PSA-$A_2M$. The correlation between the loss of immunoreactive PSA (X) and PSA-$A_2M$ formed (Y): Y=−7.81+1.07 X, r=0.99.

Validation of the immunoassay for PSA-A2M. When purified PSA was incubated with A$_2$M at 37° C., the concentrations of PSA-A$_2$M measured by the assay for PSA-A$_2$M increased with time while the concentration of free PSA decreased (FIG. 1). The loss of free PSA (X) correlated with the concentration of PSA-A$_2$M formed (Y) (FIG. 7, Y=−7.81+1.07 X, r=0.99).

Figure 8:
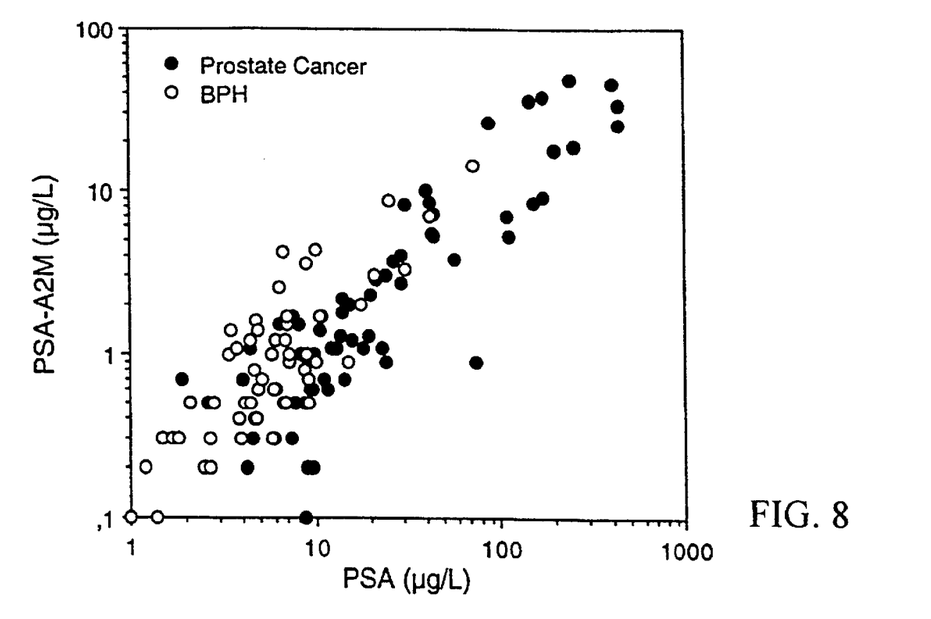
FIG. 8 shows the concentration of PSA-$A_2M$ in serum from patients with BPH (n=58) and PCa (n=73) as a function of the concentration of total PSA. The concentration of total PSA was determined by the IFMA for total PSA and that of PSA-$A_2M$ was analysed by the assay for PSA-$A_2M$.
Figure 9:
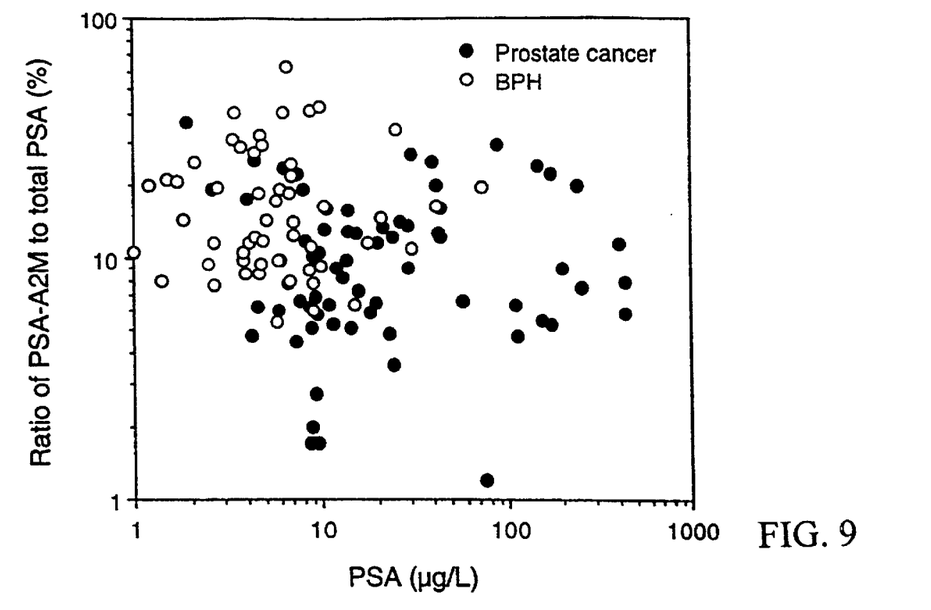
FIG. 9 shows the ratio of PSA-$A_2M$ in relation to total PSA in serum from patients with BPH (n=58) and PCa (n=73) as a function of the concentration of total PSA. The concentrations of total PSA and PSA-$A_2M$ were determined by the PSA IFMA and the novel assay for PSA-$A_2M$, respectively.
Figure 10:
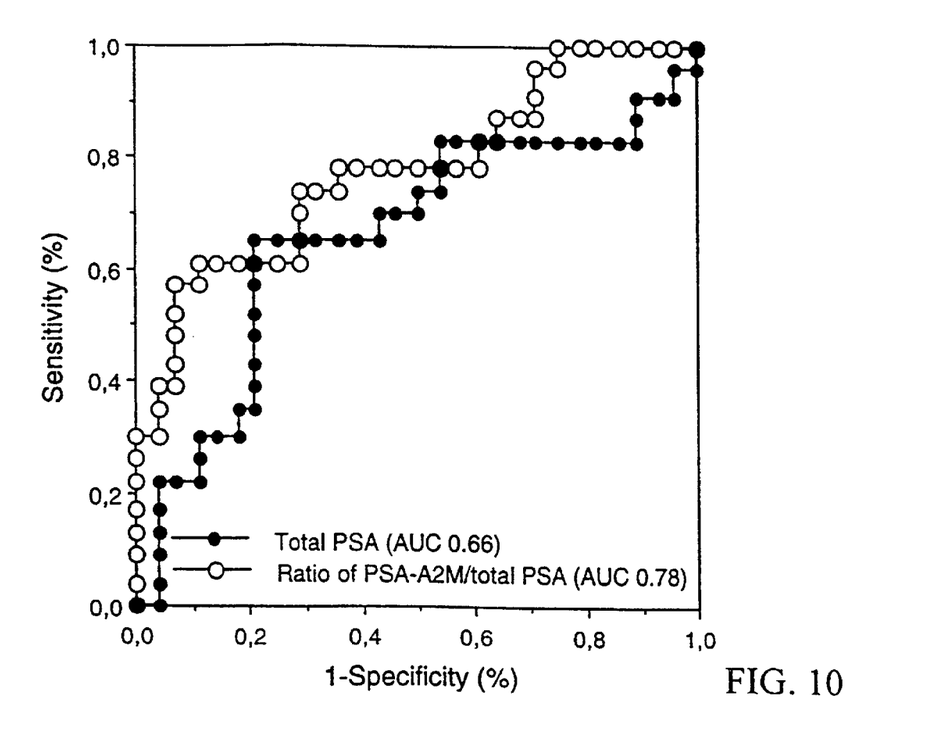
FIG. 10 shows receiver operating characteristic curves of total PSA and the ratio of PSA-$A_2M$ in serum with concentrations of total PSA between 4 and 10 μg/L. The area under the curve (AUC) was 0.78 for the ratio of PSA-$A_2M$ to total PSA and that for total PSA was 0.66.

Determination of PSA-A2M and Total PSA in Serum From Normal Females, PCa and BPH Patients The concentration of PSA-A$_2$M was below the detection limit of the assay in 44 (96%) of the 46 female sera. Two samples had apparent PSA-A$_2$M concentrations of 0.18 and 0.43 μg/L. The female serum used as a matrix for the calibration had no detectable PSA immunoreactivity as determined by the IFMA for PSA. The median concentration of total PSA was 13.5 μg/L (range 0.4–432 μg/L) in sera from 73 patients with PCa and that was 4.9 μg/L (range 1–73 μg/L) in sera of 58 BPH patients (p=0.001). In patients with PCa the concentrations of PSA-A$_2$M ranged from 0 to 49 (median 1.2) μg/L and in BPH from 0 to 14 (median 0.7 μg/L, p<0.001). The PSA-A$_2$M concentrations correlated with those of total PSA both in PCa and BPH (FIG. 8). The ratio of PSA-A$_2$M in relation to total PSA was higher in BPH (median 17%, range 0–60%) than in PCa (median 12%, range 0–63%, p<0.001, FIG. 9). In samples with PSA levels of 4–10 μg/L, the median ratio of PSA-A$_2$M to total PSA in serum was also significantly higher in BPH (19.5%, n=28) than in PCa (14.5%, n=23, p=0.002). ROC curve analysis of samples with PSA concentrations in the range 4–10 μg/L showed that the area under the curve (AUC) was 0.78 for the ratio of PSA-A$_2$M to total PSA whereas that for total PSA was 0.66 (FIG. 10).

Determination of PSA-A$_2$M, free PSA and Total PSA in Serum From a Subgroup of PCa and BPH Patients The results presented in this study concern patients with PSA concentration ranging from 4 to 20 μg/L in serum (41 PCa and 43 BPH).

Figure 11:
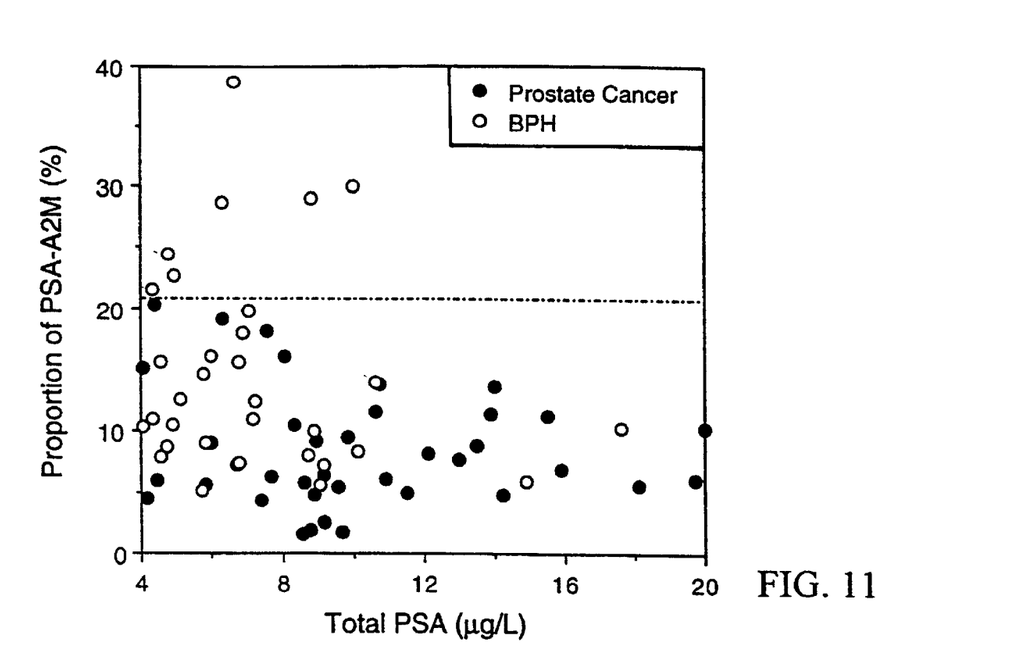
FIG. 11 shows the ratio of PSA-$A_2M$ to total PSA in serum with PSA in the range of 4–20 μg/L from patients with PCa (n=41) and BPH (n=43) as a function of total PSA concentration. The proportion of PSA-$A_2M$ was calculated by dividing PSA-$A_2M$ with the total immunoassayable PSA in untreated sera.

The concentration of PSA-$A_2$M was below the detection limit of the assay in 46 female sera, which were also devoid of PSA immunoreactivity. In serum with total PSA in the range 4–20 µg/L, the median concentration of PSA-$A_2$M expressed as the proportion of the sum of total PSA and PSA-$A_2$M in serum was lower (7%, range 2–20%) in prostate cancer than in BPH (12%, range 5–39%, p=0.0003). The median proportion of free to total PSA was also lower in prostate cancer (13%, range 6–33) than in BPH (26%, 8–52, p<0.0001). The proportion of PSA-$A_2$M decreased with increasing PSA concentrations both in patients with BPH and prostate cancer (FIG. 11).

Figure 12:
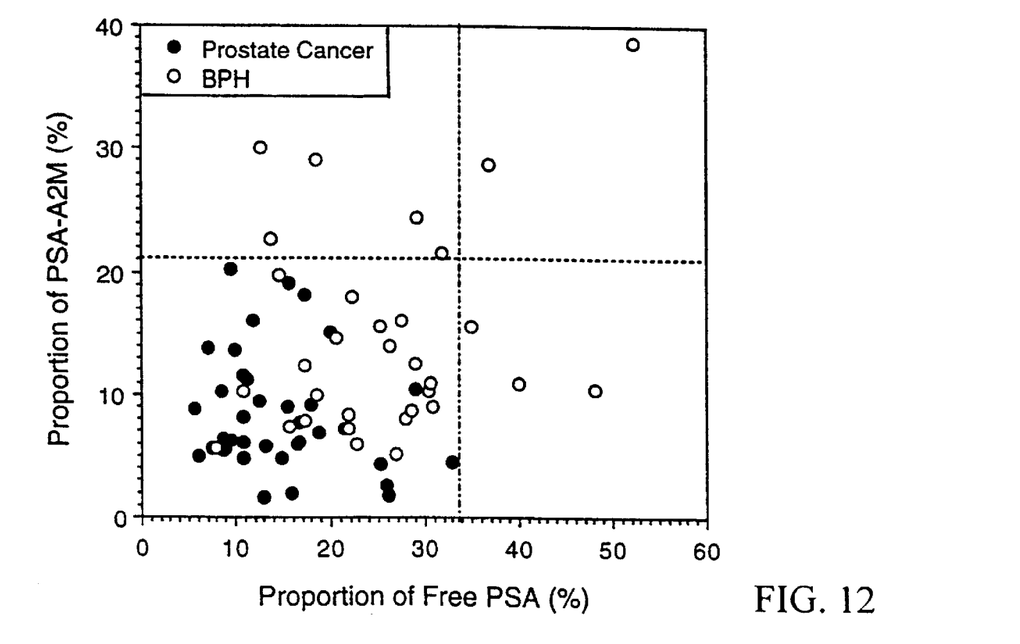
FIG. 12 shows the ratio of PSA-$A_2M$ to total PSA in sera with PSA concentrations of 4–20 μg/L from patients with prostate cancer (n=41) and BPH (n=44) as a function of the proportion of free to total PSA. The proportion of PSA-$A_2M$ was calculated as indicated in FIG. 11. The proportion of free PSA was calculated by dividing free PSA with total PSA.
Figure 13:
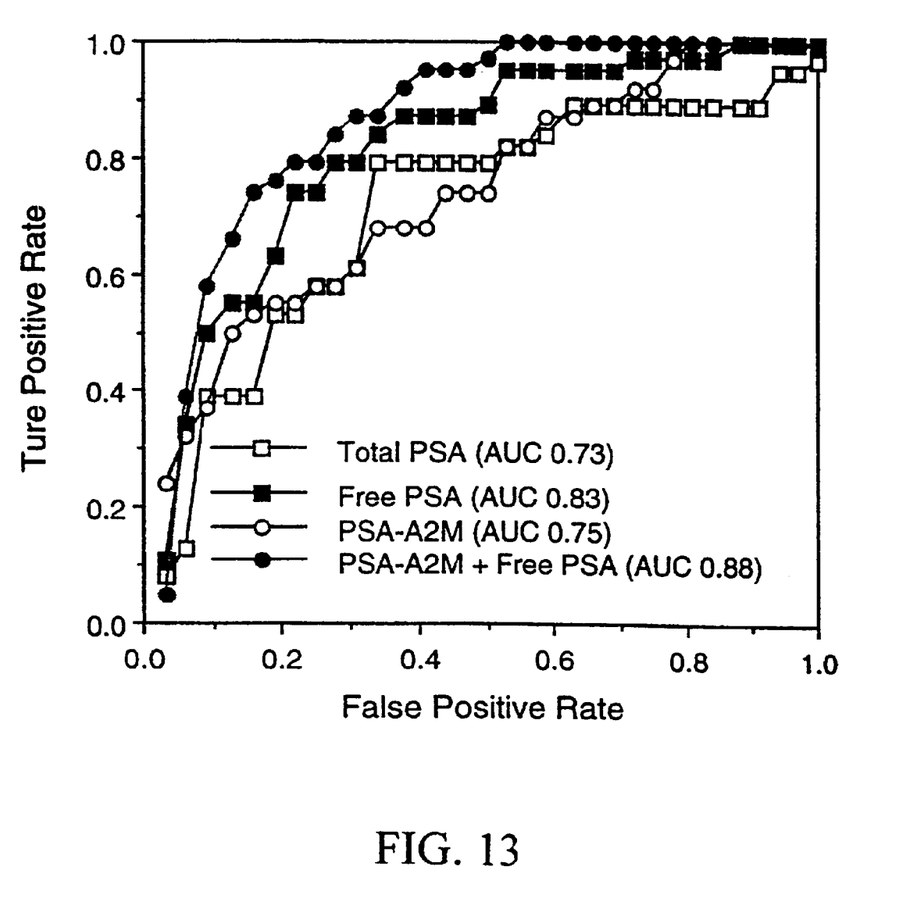
FIG. 13 shows receiver-operating characteristic (ROC) curves analysis of the proportions of PSA-$A_2M$ plus free PSA, free to total PSA and PSA-$A_2M$ and the concentration of total PSA in serum with a PSA range of 4–20 μg/L. AUC was 0.88 for the proportion of PSA-$A_2M$ plus free PSA, i.e. the ratio ((PSA-$A_2M$)+free PSA)/total PSA. AUC was 0.83 for the ratio free PSA/total PSA, 0.75 for the proportion of PSA-$A_2M$, i.e. the ratio (PSA-$A_2M$)/total PSA and 0.73 for the concentration of total PSA.

There was an inverse relationship between the proportions of free to total PSA and PSA-$A_2$M in both patient groups and this was especially notable in the BPH group. Thus many patients with BPH and a low proportion of free to total PSA suggesting a high likelihood of prostate cancer (Stenman 1991; Christensson, 1993), had a high proportion of PSA-$A_2$M. By combination of these characteristics a fairly large proportion of BPH patients with a PSA in the concentration range 4–20 µg/l could be classified as false positives (FIG. 12). The value of the combination of the two results was evaluated by calculating the proportions of PSA-$A_2$M plus free PSA, i.e. the ratio ((PSA-$A_2$M)+free PSA)/total PSA. Receiver operating characteristics analysis showed that the area under the curve for differentiation between prostate cancer and BPH (0.88) was significantly greater than that for total PSA (0.73, p=0,01). It was also greater than that of free to total PSA (0.83) (p=0.13). The area under the curve for free to total PSA was greater than that for PSA-T (p=0.11) (FIG. 13).

The diagnostic validity of the various methods and combinations of these were evaluated by logistic regression analysis. When the logarithm of the various forms of PSA were used as input variables in logistic regression, the AUC value for the combination of PSA-$A_2$M, free and total PSA was 0.86 whereas that for free and total PSA was 0.81. The AUC for total PSA alone was 0.71. PSA-$A_2$M contributed significantly to the separation between PCa and BPH (p=0.008).

When PSA is used for early detection of cancer, a cut-off giving high sensitivity is applied in order not to miss cancer cases (32). We therefore calculated the improvement in specificity at cut-off levels giving sensitivity between 90 and 100%. The proportion of PSA-$A_2$M plus free PSA gave significantly better specificity than that of free to total PSA at 100% sensitivity (p<0.05) and better than total PSA at 90–100% sensitivity (p<0.05). By using the proportion of free to total PSA plus that of PSA-$A_2$M, 18 false positive BPH cases (47%, p=0.007) could be eliminated without loss of sensitivity as compared to total PSA. Use of free to total eliminated 5 cases (16%, p=0.13).

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1) Wang M C, Valenzuela L A, Murphy G P, Chu T M. Purification of a human prostate-specific antigen. Invest Urol. 1979;17:159–63.
2) Watt K W, Lee P J, M'Timkulu T, Chan W P, Loor R. Human prostate-specific antigen: structural and functional similarity with serine proteases. Proc Natl Acad Sci USA 1986;83:3166–70.
3) Schaller J, Akiyama K, Tsuda R, Marti T, Rickli E E. Isolation, characterization and amino-acid sequence of γ-seminoprotein, a glycoprotein from human seminal plasma. Eur J Biochem 1987;170:111–30.
4) Lundwall A, Lilja H. Molecular cloning of human prostate-specific antigen cDNA. FEBS Lett 1987;214:317–22.
5) Henttu P, Vihko P. cDNA coding for the entire human prostate-specific antigen shows high homologies to the human tissue kallikrein genes. Biochem Biophys Res Commun. 1989;160:903–10.
6) Christensson A, Laurell C B, Lilja H. Enzymatic activity of prostate-specific antigen and its reactions with extracellular serine proteinase inhibitors. Eur J Biochem 1990;194:755–63.
7) Christensson A, Lilja H. Complex formation between protein C inhibitor and prostate-specific antigen in vitro and in human semen. Eur J Biochem 1994;220:45–53.
8) Leinonen J, Zhang W-M, Stenman U-H. Complex formation between PSA isoenzymes and protease inhibitors. J Urol 1996;155:1099–103.
9) Zhang W-M, Leinonen J, Kalkkinen N, Stenman U-H. Prostate-specific antigen forms a complex with and cleaves alpha1-protease inhibitor in vitro. Prostate 1997;33:87–96.
10) Stenman U-H, Leinonen J, Alfthan H, Rannikko S, Tuhkanen K, Alfthan 0. A complex between prostate-specific antigen and alpha1-antichymotrypsin is the major form of prostate-specific antigen in serum of patients with prostatic cancer: assay of the complex improves clinical sensitivity for cancer. Cancer Res 1991;51:222–6.
11) Lilja H, Christensson A, Dahlen U, Matikainen M T, Nilsson O, Pettersson K, Lövgren T. Prostate-specific antigen in serum occurs predominantly in complex with alpha-1-antichymotrypsin. Clin Chem 1991;37:1618–25.
12) Zhang W-M, Finne P, Leinonen J, Vesalainen S, Nordling S, Stenman U-H. Measurement of the complex between prostate-specific antigen and alpha1-protease inhibitor in serum. Clin Chem 1998; (submitted).
13) Pettersson K, Piironen T, Seppälä M, Liukkonen L, Christensson A, Matikainen MT, et al. Free and complexed prostate-specific antigen (PSA): in vitro stability, epitope map, and development of immunofluorometric assays for specific and sensitive detection of free PSA and PSA-alpha 1-antichymotrypsin complex. Clin Chem 1995;41:1480–8.
14) Leinonen J, Lövgren T, Vornanen T, Stenman U-H. Double-lable time-resolved immunofluorometric assay of prostate-specific antigen and of its complex with alpha-1-antichymotrypsin. Clin Chem 1993;39:2098–103.
15) Christensson A, Björk T, Nilsson O, Dahlen U, Matikainen MT, Cockett AT, et al. Serum prostate-specific antigen complexed to alpha1-antichymotrypsin as an indicator of prostate cancer. J Urol 1993;150:100–5.
16) Barrett A J, Brown M A, Sayers C A. The eletrophoretically 'slow' and 'fast' forms of the alpha-2-macroglobulin molecule. Biochem J 1979;181:401–18.
17) Sottrup-Jensen L. Alpha-macroglobulins: Structure, shape, and mechanism of proteinase complex formation. J Biol Chem 1989;264:11539–42.
18) Barrett A J, Starkey P M. The interaction of alpha-2-macroglobulin with proteinases: Characteristics and specificity of the reaction and a hypothesis concerning its molecular mechanism. Biochem J 1973;133:709–24.
19) Miyata K, Nakamura M, Tomoda K. Interaction between serratia protease and human plasma alpha-2-macroglobulin. J Biochem 1981;89:1231–7.

20) Zhou A M, Tewari P C, Bluestein B I, Caldwell G W, Larsen F L. Multiple forms of prostate-specific antigen in serum: differences in immunorecognition by monoclonal and polyclonal assays. Clin Chem 1993;39:2483–91.
21) Zhang W-M, Leinonen J, Kalkkinen N, Dowell B, Stenman U-H. Purification and characterization of different molecular forms of prostate-specific antigen in human seminal fluid. Clin Chem 1995;41:1567–73.
22) Kurecki T, Kress L F, Laskowski M. Purification of human alpha-2-macroglobulin and alpha-1-proteinase inhibitor using zinc chelate chromatography. Anal Biochem 1979;99:415–20.
23) Laemmli U K. Cleavage of structure proteins during the assemble of the head bacteriophage T4. Nature 1970;227:680–5.
24) Towbin H, Staehelin T. Gordon J. Electrophoretic transfer of proteins from polyacrylamide gels to nitrocellulose sheets: procedure and some applications. Proc Natl Acad Sci USA 1979;76:4350–4.
25) Stenman U-H, Hakama M, Knekt P, Aromaa A, Teppo L, Leinonen J. Serum concentrations of prostate-specific antigen and its complex with alpha1-antichymotrypsin before diagnosis of prostate cancer. Lancet 1994;344:1594–8.
26) Platt E J, Karlsen K, Lopez-Valdivieso A, Cook P W, Firestone G L. High sensitive immunoadsorption procedure for detection of low-abundance proteins. Anal Biochem 1986;156:126–35.
27) Espana F, Sanchez C J, Estelles A, Gilabert J, Griffin J H, Heeb M J. Quantitative immunoassay for complexes of prostate-specific antigen with alpha-2-macroglobulin. Clin Chem 1996;42:545–50.
28) Stamey T A, Yang N, Hay A R, McNeal J E, Freiha F S, Redwine E. Prostate-specific antigen as a serum marker for adenocarcinoma of the prostate. N Engl J Med 1987;317:909–16.
29) Oesterling J E, Chan D W, Epstein J I, Kimball A W, Bruzek D J, Rock R C, et al. Prostate specific antigen in the preoperative and postoperative evaluation of localized prostatic cancer treated with radical prostatectomy. J Urol 1988;139:766–72.
30) Lilja H and Stenman U H, WO 92/01936, published Feb. 6, 1992.
31) Pettersson K, Piironen T and Lilja H. A sensitive serum assay for prostate specific antigen (PSA) in complex with alpha-2-macroglobulin (AMG)—a possible diagnostic tool in prostate related disorders. Eur Urol 1998:33 (Suppl 1):64).
32) Catalona W, Hudson M, Scardino P, Richie J, Ahmann F, Flanigan R, deKernion J, Ratliff T, Kavoussi L, Dalkin B, et al. Selection of optimal prostate specific antigen cutoffs for early detection of prostate cancer: receiver operating characteristic curves. J Urol. 1994; 152:2037–42.

What is claimed is:

1. An immunoassay for quantitative determination of the amount of the complex (PSA-$A_2M$) between prostate specific antigen (PSA) and $\alpha_2$-macroglobulin ($A_2M$) in a serum sample in which the PSA concentration is between about 2 µg/L and about 20 µg/L, comprising the steps of removing a first immunoreactive PSA from said sample by immunoadsorption of the first immunoreactive PSA to produce a supernatant containing a PSA-$A_2M$ complex, treating the PSA-$A_2M$ complex in the supernatant to denature the PSA-$A_2M$ complex to produce a second immunoreactive PSA, determining the second immunoreactive PSA by contacting the second immunoreactive PSA with an antibody which specifically binds the second immunoreactive PSA, and detecting the second immunoreactive PSA bound to the antibody.

2. The assay according to claim 1, wherein the denaturation of the complex is performed by raising the pH of the supernatant to the range of 10.5 to 12.

3. The assay according to claim 1, wherein the sample is from a male individual, the antibody is labeled and the serum concentration of the PSA-$A_2M$ complex is determined by comparison with a standard curve for an in vitro PSA-$A_2M$ complex.

4. The assay according to claim 1, wherein the second immunoreactive PSA is determined by a sandwich assay using two monoclonal antibodies which specifically binds the second immunoreactive PSA.

5. The assay according to claim 2, wherein the pH is 11.5.

6. The assay according to claim 2, wherein the pH is raised by the addition of NaOH.

7. The assay according to claim 6, wherein the pH is raised by the addition of NaOH.

8. The assay according to claim 2, wherein the sample is from a male individual, the antibody is labeled and the serum concentration of the PSA-$A_2M$ complex is determined by comparison with a standard curve for an in vitro PSA-$A_2M$ complex.

9. The assay according to claim 2, wherein the second immunoreactive PSA is determined by a sandwich assay using two monoclonal antibodies which specifically binds the second immunoreactive PSA.

10. The assay according to claim 5, wherein the sample is from a male individual, the antibody is labeled and the serum concentration of the PSA-$A_2M$ complex is determined by comparison with a standard curve for an in vitro PSA-$A_2M$ complex.

11. The assay according to claim 5, wherein the second immunoreactive PSA is determined by a sandwich assay using two monoclonal antibodies which specifically binds the second immunoreactive PSA.

12. The assay according to claim 6, wherein the sample is from a male individual, the antibody is labeled and the serum concentration of the PSA-$A_2M$ complex is determined by comparison with a standard curve for an in vitro PSA-$A_2M$ complex.

13. The assay according to claim 6, wherein the second immunoreactive PSA is determined by a sandwich assay using two monoclonal antibodies which specifically binds the second immunoreactive PSA.

14. The assay according to claim 7, wherein the sample is from a male individual, the antibody is labeled and the serum concentration of the PSA-$A_2M$ complex is determined by comparison with a standard curve for an in vitro PSA-$A_2M$ complex.

15. The assay according to claim 8, wherein the second immunoreactive PSA is determined by a sandwich assay using two monoclonal antibodies which specifically binds the second immunoreactive PSA.

* * * * *